US00PP15125P2

(12) United States Plant Patent
Redman

(10) Patent No.: US PP15,125 P2
(45) Date of Patent: Aug. 31, 2004

(54) CHRYSANTHEMUM PLANT NAMED 'PADMOS TIME PINK'

(50) Latin Name: *Chrysanthemum morifolium*
Varietal Denomination: Padmos Time Pink

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/364,267

(22) Filed: Feb. 10, 2003

(51) Int. Cl.[7] ..... A01H 5/00
(52) U.S. Cl. ..... Plt./291
(58) Field of Search ..... Plt./291

(56) References Cited

PUBLICATIONS

1996 Ficor catalog, listing the variety 'Cerise About Time,' published Sep. 1995. See, e.g., pp. 2 and 9, (no photograph).

2001 CBA (Chrysanthemum Breeders Association) catalogue excerpt listing the variety "Patterson." See p. 16 (no photograph).

2002 CBA (Chrysanthemum Breeders Association) catalogue excerpt listing the variety "Patterson." (Best copy available, no photograph).

2003 CBA (Chrysanthemum Breeders Association) catalogue listing the variety "Patterson." See, e.g., pp. 17 and 18 (color photograph).

2003–2004 Van Zanten Cuttings B.V. catalog for "Pot plants and Bedding plants," listing the variety 'Patterson,' published Sep. 1, 2003. See, e.g., pp. 41 (color photograph) and 42.

*Primary Examiner*—Anne Marie Grunberg
(74) *Attorney, Agent, or Firm*—Howrey Simon Arnold & White, LLP

(57) ABSTRACT

A new variety of Chrysanthemum plant named 'Padmos Time Pink,' having a good uniform canopy of pink decorative flowers. The new variety has a tall vigor, free branching, uniform spreading habit and a good foliage presentation.

1 Drawing Sheet

Latin name of the genus and species: Botanical classification: *Chrysanthemum morifolium.*

Variety denomination: The new Chrysanthemum variety denomination is 'Padmos Time Pink.'

BACKGROUND OF THE INVENTION

The present invention comprises a new and distinct cultivar of Chrysanthemum botanically known as *Chrysanthemum morifolium,* and referred to by the cultivar name 'Padmos Time Pink.'

'Padmos Time Pink,' identified as 20546-0, originated from a cross made in a controlled breeding program in Chichester, West Sussex, United Kingdom. The female parent of the new variety is an undistributed, unpatented seedling identified as 20002-26 of the variety known as 'About Time Cerise.' The male parent of the new variety is an undistributed, seedling identified as 'Delano' (U.S. Plant Pat. No. 6,950). The new variety 'Padmos Time Pink' has been asexually reproduced by vegetative cuttings in Chichester, West Sussex, United Kingdom and the distinguishing characteristics are retained through successive generations of asexual reproduction.

BRIEF SUMMARY OF THE INVENTION

'Padmos Time Pink' is a pot type of Chrysanthemum plant variety having pink decorative flowers.

Comparison with Female Parent

Plants of the new Chrysanthemum variety 'Padmos Time Pink' are dissimilar to the parent cultivar 'About Time Cerise' in plant habitat and growth rate. In side-by-side comparisons in Chichester, West Sussex, United Kingdom, under commercial practice, plants of the new Chrysanthemum variety 'Padmos Time Pink' differed from the plants of the parent cultivar 'About Time Cerise' in the following characteristics.

1. The new variety 'Padmos Time Pink' produces pink decorative flowers whereas the parent cultivar 'About Time Cerise' produces dark pink flowers.
2. Plants of the new variety 'Padmos Time Pink' have taller and larger inflorescence than plants of the parent cultivar 'About Time Cerise.'

Comparison with Male Parent

Plants of the new Chrysanthemum variety 'Padmos Time Pink' are dissimilar to the parent cultivar 'Delano' in plant habitat and growth rate. In side-by-side comparisons in Chichester, West Sussex, United Kingdom, under commercial practice, plants of the new Chrysanthemum variety 'Padmos Time Pink' differed from the plants of the parent cultivar 'Delano' in the following characteristics.

1. The new variety 'Padmos Time Pink' produces pink decorative flowers whereas the parent cultivar 'Delano' produces red flowers.
2. Plants of the new variety 'Padmos Time Pink' have taller and larger inflorescence than plants of the parent cultivar 'Delano.'

Comparison with Other Varieties

Plants of the new Chrysanthemum variety 'Padmos Time Pink' are similar to the cultivar 'Patterson' in plant habit and growth rate. However in side-by-side comparisons in Chichester, West Sussex, United Kingdom, under commercial practice, plants of the new Chrysanthemum variety 'Padmos Time Pink' differed from plants of the cultivar 'Patterson' in the following characteristics.

1. The new variety 'Padmos Time Pink' produces salmon pink decorative flowers whereas the cultivar 'Patterson' produces light pink decorative flowers.
2. Plants of the new variety 'Padmos Time Pink' have larger and taller inflorescence than plants of the cultivar 'Patterson.'

BRIEF DESCRIPTION OF ILLUSTRATION

Typical specimens of the plant and flowers for the new Chrysanthemum variety 'Padmos Time Pink' are shown in the accompanying digital photograph. The colors shown are as true as possible within the usual limits of this kind of illustration.

FIG. 1 is a whole plant view of the new variety 'Padmos Time Pink' grown in a pot. The plant shown in the illustration is 54 days from the commencement of Short Days.

DETAILED BOTANICAL DESCRIPTION

The following description of the new Chrysanthemum variety 'Padmos Time Pink' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 25 days with a response time of about 7.5 weeks. The new variety is suitable for growth in a temperature range of 15° C. to 25° C.

The new variety may be produced as a spray. The following description is with respect to a plant produced as a pot Chrysanthemum. In the description of this new Chrysanthemum variety, color values have been taken from The Royal Horticultural Society Colour Chart (R.H.S.C.C.).

Plant

Plant type: Pot.
Habit: Upright and free branching.
Height: 26 cm.
Width: 35 cm.
Branching characteristics: Upright and free branching.
Length of lateral branches: 19 cm.
Number of breaks from pinch: 5.
Stem color: 138B.
Response time: 52 days.
Vigor: Tall.
Shelf life: 25 days.
Disease/pest (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 Long Days the first roots emerge and form root primordia. In 14 days a complete root system is developed.

Foliage

Number of leaves per lateral branch: 10.
Compound or single: Single.
Arrangement of leaves: Alternate.
*Shape of leaf.*—Typically 5 lobed ovate.
*Size of leaf.*—Width (cm): 6.5. Length (cm): 10.
*Leaf apex.*—Acute.
*Base.*—Obtuse.
*Attachment.*—Petioled.
*Aspect.*—Slight undulating.
*Margin.*—Palmately lobed.
*Surface characteristics.*—Top: slightly pubescent. Bottom: pubescent.
Petiole: Color: 147C. Length: 2.4 cm.
Venation: Net prominent mid-vein at underside. Color: Upper side: near 137C. Under side: near 138B.
Color: Mature Leaf, upper side: near 137A; under side: near 138B. Young Leaf, upper side: near 147A; under side: near 137A.

Flower

Flower appearance: Matte.
Flower type: Decorative.
Flower form: Domed.
Flower shape: Round.
Flowering habit: Cyme.
Number of blossoms per branch: 5.
Inflorescence form: Cyme.
*Depth of fully expanded blossoms.*—2 cm.
*Diameter of fully expanded blossoms.*—6 cm.
Phyllaries:
*Number.*—14.
*Color.*—Near 138A.
*Length.*—1 cm.
*Width.*—0.2 cm.
*Texture/appearance.*—Pubescent.
Peduncle: Peduncle length is shortest at the terminal flower and progressively longer moving down the stem.
*Length.*—11 cm (average).
*Color.*—Near 138B.
*Surface.*—Pubescent.
*Habit.*—Slightly undulating.
*Strength.*—Medium.
Pedicel: Length: terminal: 3 cm; lateral: 4.5 cm.
*Color.*—Near 138B.
*Surface.*—Pubescent.

*Habit.*—Slightly undulating.
*Strength.*—Medium.
Ray florets:
*Form/shape.*—Straight.
*Texture/appearance.*—Matte.
*Number per flower.*—90.
*Length.*—3.5 cm; Width: 1 cm.
*Apex.*—Rounded.
*Base.*—Tapered.
*Margin.*—Entire.
Disc florets:
*Form/shape.*—Cylindric.
*Texture/appearance.*—Shiny.
*Number per flower.*—10.
*Length.*—0.6 cm; Width: 0.1 cm.
*Diameter of disc.*—0.4 cm.
Fragrance: None.
Flower bud (at onset of color):
*Length.*—1.5 cm.
*Diameter.*—1 cm.
*Form/shape.*—Spherical.
General flower color:
1. *Ray florets, upper side.*—Immature: near 73B. Mature: near 73C. Older/fading: near 73D.
2. *Ray florets, under side.*—Immature: near 73C. Mature: near 73C. Older/fading: near 73D.
3. *Disc florets.*—Immature: near 145B. Mature: near 145B. Older/fading: near 145C.
4. *Bud.*—73C.

Flower progression with age: Flower form does not change but there is a slight colour fading with age.

Reproductive Organs

Gynoecium: Present on Ray and Disc florets.
Ray florets per individual flower:
*Pistil number.*—90.
*Stigma color.*—Near 154A.
*Stigma shape.*—Forked.
*Style color.*—Near 154B.
*Style length.*—0.3 cm.
Disc florets:
*Pistil number.*—10.
*Stigma color.*—Near 154A.
*Stigma shape.*—Forked.
*Style color.*—Near 154A.
*Style length.*—0.3 cm.
Androecium: Not observed.
Lastingness of bloom: About 25 days.
Fruit and seeds: None observed.

What is claimed is:

1. A new and distinct variety of Chrysanthemum plant, substantially as described and illustrated herein.

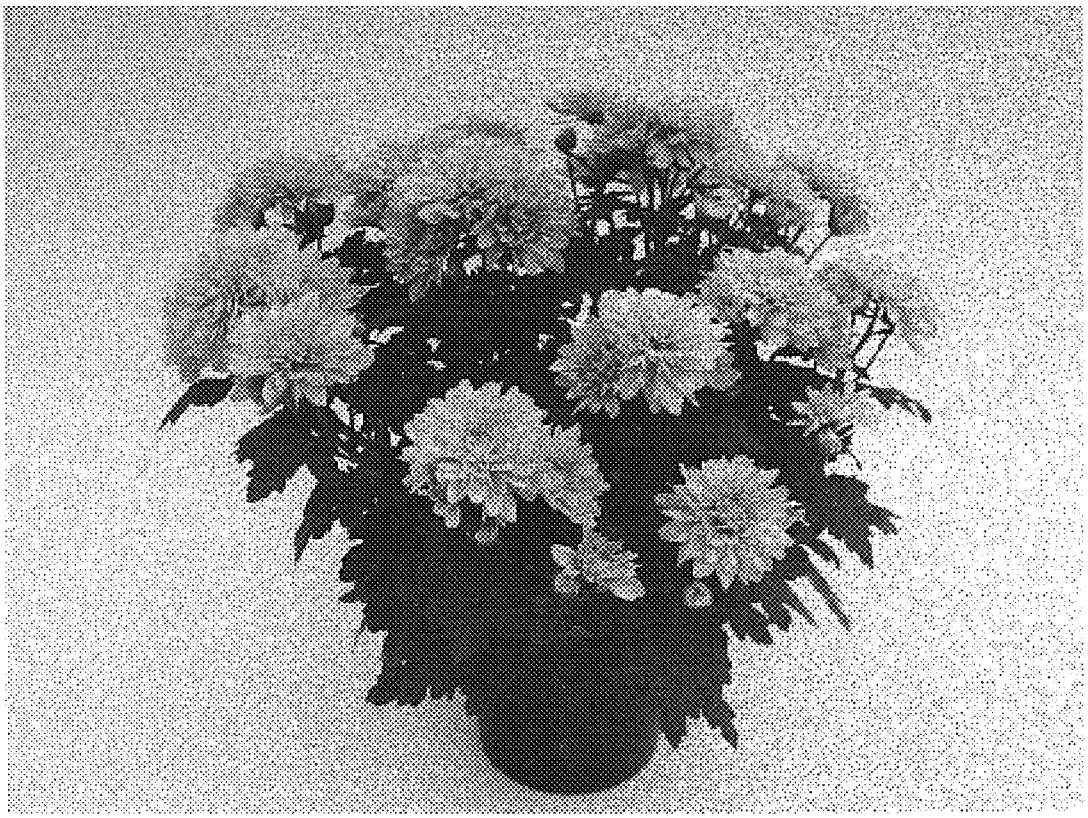

* * * * *